(12) United States Patent
Koktzoglou et al.

(10) Patent No.: US 8,744,551 B2
(45) Date of Patent: Jun. 3, 2014

(54) METHOD FOR NON-CONTRAST ENHANCED MAGNETIC RESONANCE ANGIOGRAPHY

(75) Inventors: Ioannis Koktzoglou, Des Plaines, IL (US); Robert R. Edelman, Highland Park, IL (US)

(73) Assignee: Northshore University Healthsystem, Evanston, IL (US)

(*) Notice: Subject to any disclaimer, the term of this patent is extended or adjusted under 35 U.S.C. 154(b) by 42 days.

(21) Appl. No.: 13/547,699

(22) Filed: Jul. 12, 2012

(65) Prior Publication Data

US 2014/0018666 A1 Jan. 16, 2014

(51) Int. Cl.
*A61B 5/05* (2006.01)

(52) U.S. Cl.
USPC .......................................... 600/419; 600/410

(58) Field of Classification Search
USPC .................................. 600/407–430
See application file for complete search history.

(56) References Cited

U.S. PATENT DOCUMENTS

| | | | | |
|---|---|---|---|---|
| 6,043,655 A | * | 3/2000 | Makita et al. | 324/309 |
| 7,283,862 B1 | * | 10/2007 | Slavin et al. | 600/420 |
| 7,328,054 B2 | * | 2/2008 | Jesmanowicz | 600/410 |
| 7,545,141 B2 | * | 6/2009 | Kimura | 324/306 |
| 8,332,010 B2 | | 12/2012 | Edelman | |
| 2004/0162483 A1 | * | 8/2004 | Kimura | 600/419 |
| 2010/0268062 A1 | | 10/2010 | Edelman | |

OTHER PUBLICATIONS

Mistretta, Sub-Nyquist Acquisition and Constrained Reconstruction in Time Resolved Angiography, Med. Phys., 2011, 38(6):2975-2985.
Moftakhar, et al., Noninvasive Measurement of Intra-Aneurysmal Pressure and Flow Pattern Using Phase Contrast with Vastly Undersampled Isotropic Projection Imaging, AJNR, 2007, 28(9):1710-1714.
Nielsen, et al., Improved 2D Time-of-Flight Angiography Using a Radial-Line k-space Acquisition, Magnetic Resonance in Medicine, 1997, 37:285-291.
Nielsen, et al., Ultra-Short Echo-Time 2D Time-of-Flight MR Angiography Using a Half-Pulse Excitation, Magnetic Resonance in Medicine, 1999, 41:591-599.
Peters, et al., High-Resolution MRI of Cardiac Function With Projection Reconstruction and Steady-State Free Precession, Magnetic Resonance in Medicine, 2002, 48(1):82-88.
Schreiber, et al., Dynamic Contrast-Enhanced Myocardial Perfusion Imaging Using Saturation-Prepared TrueFISP, Journal of Magnetic Resonance Imaging, 2002, 16(6):641-652.

(Continued)

*Primary Examiner* — Sanjay Cattungal
(74) *Attorney, Agent, or Firm* — Quarles & Brady, LLP (57) ABSTRACT

A method for non-contrast enhanced magnetic resonance angiography (MRA) of a three-dimensional (3D) volume of a subject having a vascular structure extending through the 3D volume and having flowing spins passing through vascular structure. The method includes applying at least one radiofrequency (RF) pulse to a first slice to label the flowing spins passing into a second slice located within the 3D volume adjacent to the first slice and acquiring imaging data from the second slice using a two-dimensional (2D) pulse sequence and sampling k-space using a non-Cartesian sampling pattern. The acquisition of the of the imaging data is repeated to acquire a series of second slices located across the 3D volume to acquire respective sets of imaging data spanning the 3D volume. The sets of imaging data is reconstructed into a time-series of image frames depicting the flowing spins passing through the vascular structure.

22 Claims, 6 Drawing Sheets

(56) References Cited

OTHER PUBLICATIONS

Spuentrup, et al., Coronary MR Imaging Using Free-Breathing 3D Steady-State Free Precession with Radial k-Space Sampling, Fortschr Rontgenstr, 2003, 175(10):1330-1334.

Spuentrup, et al., Free-Breathing 3D Steady-State Free Precession Coronary MR Angiography with Radial k-Space Sampling: Comparison with Cartesian k-Space Sampling and Cartesian Gradient-Echo Coronary MR Angiography—Pilot Study, Radiology, 2004, 231:581-586.

Stehning, et al., Fast Isotropic Volumetric Coronary MR Angiography Using Free-Breathing 3D Radial Balanced FFE Acquisition, Magnetic Resonance in Medicine, 2004, 52:197-203.

Swan, et al., Time-Resolved Three-Dimensional Contrast-Enhanced MR Angiography of the Peripheral Vessels, Radiology, 2002, 225:43-52.

Swan, et al., Peripheral MR Angiography with Variable Velocity Encoding. Work in Progress., Radiology, 1992, 184:813-817.

Thornton, et al., High-Resolution, Time-Resolved MRA Provides Superior Definition of Lower-Extremity Arterial Segments Compared to 2D Time-Of-Flight Imaging, Journal of Magnetic Resonance Imaging, 2006, 24(2):362-370.

Turk, et al. Physiologic and Anatomic Assessment of a Canine Carotid Artery Stenosis Model Utilizing Phase contrast with Vastly Undersampled Isotropic Projection Imaging, AJNR Am. J. Neuroradiol., 2007, 28:111-115.

Vakil, et al., Magnetization Spoiling in Radial FLASH Contrast-Enhanced MR Digital Subtraction Angiography, Journal of Magnetic Resonance Imaging, 2012, 36(1):249-258.

Velikina, et al., PC HYPR Flow: A Technique for Rapid Imaging of Contrast Dynamics, Journal of Magnetic Resonance Imaging, 2010, 31(2):447-456.

Vigen, et al., Undersampled Projection-Reconstruction Imaging for Time-Resolved Contrast-Enhanced Imaging, Magnetic Resonance in Medicine, 2000, 43(2):170-176.

Wang, et al., Generalized Matched Filtering for Time-Resolved MR Angiography of Pulsatile Flow, Magnetic Resonance in Medicine, 1993, 30(5):600-608.

Weber, et al., Quantitative Velocity Images from Thick Slab 2D Phase Contrast, Magnetic Resonance in Medicine, 1993, 29(2):216-225.

Willig, et al., Contrast-Enhanced 3D MR DSA of the Carotid Artery Bifurcation: Preliminary Study of Comparison with Unenhanced 2D and 3D Time-Of-Flight MR Angiography, Radiology, 1998, 208:447-451.

Wu, et al., 3D Time-Resolved Contrast-Enhanced Cerebrovascular MR Angiography with Subsecond Frame Update Times Using Radial k-Space Trajectories and Highly Constrained Projection Reconstruction, AJNR Am. J. Neuoradiol., 2007, 28:2001-2004.

Wu, et al., Evaluation of Temporal and Spatial Characteristics of 2D HYPR Processing Using Simulations, Magnetic Resonance in Medicine, 2008, 59(5):1090-1098.

Wu, et al., Comparison of HYPR Stack-of-Stars and HYPR VIPR to TRICKS in Peripheral CE MRA, Proc. Intl. Soc. Mag. Reson. Med., 2008, 16:108.

Wu, et al., CE-MRA of the Lower Extremities Using HYPR Stack-of-Stars, Journal of Magnetic Resonance Imaging, 2009, 29(4):917-923.

Wu, et al., HYPR TOF: Time-Resolved Contrast-Enhanced Intracranial MR Angiography Using Time-of-Flight as the Spatial Constraint, Journal of Magnetic Resonance Imaging, 2011, 33(3):719-723.

Wu, et al., Fast Whole-Brain 4D Contrast-Enhanced MR Angiography with Velocity Encoding Using Undersampled Radial Acquisition and Highly Constrained Projection Reconstruction: Image-Quality Assessment in Volunteer Subjects, AJNR Am. J. Neuroradiol., 2011, 32:E47-E50.

Yamashita, et al., Selective Visualization of Renal Artery Using SSFP with Time-Spatial Labeling Inversion Pulse: Non-Contrast Enhanced MRA for Patients with Renal Failure, Proc. Intl. Soc. Mag. Reson. Med., 2005, 13:1715.

Amano, et al., Noncontrast-Enhanced Three-Dimensional Magnetic Resonance Aortography of the Thorax at 3.0 T Using Respiratory-Compensated T1-Weighted k-Space Segmented Gradient-Echo Imaging with Radial Data Sampling: Preliminary Study, Investigative Radiology, 2009, 44(9):548-552.

Anderson, III, et al., On the Advantages of Reetrospectively Gated Radial Acquisitions for Cine Phase Contrast Flow Imaging, Proc. Intl. Soc. Mag. Reson. Med., 2011, 19:2621.

Barger, et al., Phase-Contrast with Interleaved Undersampled Projections, Magnetic Resonance in Medicine, 2000, 43(4):503-509.

Barger, et al., Time-Resolved Contrast—Enhanced Imaging With Isotropic Resolution and Broad Coverage Using an Undersampled 3D Projection Trajectory, Magnetic Resonance in Medicine, 2002, 48:297-305.

Carroll, et al., Method for Rapidly Determining and Reconstructing the Peak Arterial Frame from a Time-Resolved CE-MRA Exam, Magnetic Resonance in Medicine, 2000, 44(5):817-820.

Carroll, et al., The Effect of Injection Rate on Time-Resolved Contrast-Enhanced Peripheral MRA, Journal of Magnetic Resonance Imaging, 2001, 14(4):401-410.

Cashen, et al., 4D Radial Contrast-Enhanced MR Angiography with Sliding Subtraction, Magnetic Resonance in Medicine, 2007, 58(5):962-972.

Chang, et al., Hemodynamic Changes in Patients with Arteriovenous Malformations Assessed Using High-Resolution 3D Radial Phase-Contrast MR Angiography, AJNR Am. J. Neuroradiol, 2012, 33:1565-1572.

Chang, et al., Velocity Measurements in the Middle Cerebral Arteries of Healthy Volunteers Using 3D Radial Phase-Contrast HYPRFlow: Comparison with Transcranial Doppler Sonography and 2D Phase-Contrast MR Imaging, AJNR, 2011, 32(1):54-59.

Du et al., Time-Resolved, Undersampled Projection Reconstruction Imaging for High-Resolution CE-MRA of the Distal Runoff Vessels, Magnetic Resonance in Medicine, 2002, 48(3):516-522.

Du, et al., SNR Improvement for Multiinjection Time-Resolved High-Resolution CE-MRA of the Peripheral Vasculature, Magnetic Resonance in Medicine, 2003, 49(5):909-917.

Du, et al., Noise Reduction in MR Angiography with Nonlinear Anisotropic Filtering, Journal of Magnetic Resonance Imaging, 2004, 19(5):632-639.

Du, et al., Artifact Reduction in Undersampled Projection Reconstruction MRI of the Peripheral Vessels Using Selective Excitation, Magnetic Resonance in Medicine, 2004, 51(5):1071-1076.

Du, et al., High-Resolution Multistation Peripheral MR Angiography Using Undersampled Projection Reconstruction Imaging, Magnetic Resonance in Medicine, 2004, 52(1):204-208.

Du, et al., Contrast-Enhanced Peripheral Magnetic Resonance Angiography Using Time-Resolved Vastly Undersampled Isotropic Projection Reconstruction, Journal of Magnetic Resonance Imaging, 2004, 20(5):894-900.

Du, et al., Time-Resolved Undersampled Projection Reconstruction Magnetic Resonance Imaging of the Peripheral Vessels Using Multi-Echo Acquisition, Magnetic Resonance in Medicine, 2005, 53(3):730-734.

Du, et al., Dynamic MR Venography: An Intrinsic Benefit of Time-Resolved MR Angiography, Journal of Magnetic Resonance Imaging, 2006, 24(4):922-927.

Du, et al., Time-Resolved Contrast-Enhanced Carotid Imaging Using Undersampled Projection Reconstruction Acquisition, Journal of Magnetic Resonance Imaging, 2007, 25(5):1093-1099.

Du, et al., Whole-Body MR Angiography Using Variable Density Sampling and Dual-Injection Bolus-Chase Acquisition, Magnetic Resonance Imaging, 2008, 26(2):181-187.

Du, et al., Contrast-Enhanced MR Angiography Using Time Resolved Interleaved Projection Sampling with Three-Dimensional Cartesian Phase and Slice Encoding (TRIPPS), Magnetic Resonance in Medicine, 2009, 61(4):918-924.

Eddleman, et al., 4D Radial Acquisition Contrast-Enhanced MR Angiography and Intracranial Arteriovenous Malformations Quickly Approaching Digital Subtraction Angiography, Stroke, 2009, 40:2749-2753.

(56) References Cited

OTHER PUBLICATIONS

Fain, et al., Floating Table Isotropic Projection (FLIPR) Acquisition: A Time-Resolved 3D Method for Extended Field-of-View MRI During Continuous Table Motion, Magnetic Resonance in Medicine, 2004, 52(5):1093-1102.
Francois, et al., Renal Arteries: Isotropic, High-Spatial-Resolution, Unenhanced MR Angiography with Three-Dimensional Radial Phase Contrast, Radiology, 2011, 258(1):254-260.
Frayne, et al., MR Angiography with Three-Dimensional MR Digital Subtraction Angiography, Topics in Magnetic Resonance Imaging, 1996, 8(6):366-388.
Frayne, et al., 3D MR DSA: Effects of Injection Protocol and Image Masking, Journal of Magnetic Resonance Imaging, 2000, 12(3):476-487.
Ge, et al., Myocardial Perfusion MRI with Sliding-Window Conjugate-Gradient HYPR, Magnetic Resonance in Medicine, 2009, 62(4):835-839.
Gu, et al., PC VIPR: A High-Speed 3D Phase-Contrast Method for Flow Quantification and High-Resolution Angiography, AJNR Am. J. Neuroradiol., 2005, 26:743-749.
Jahnke, et al., Comparison of Radial and Cartesian Imaging Techniques for MR Coronary Angiography, Journal of Cardiovascular Magnetic Resonance, 2004, 6(4):865-875.
Johnson, et al., Improved Waveform Fidelity Using Local HYPR Reconstruction (HYPR LR), Magnetic Resonance in Medicine, 2008, 59(3):456-462.
Johnson, et al., Improved 3D Phase Contrast MRI with Off-Resonance Corrected Dual Echo VIPR, Magnetic Resonance in Medicine, 2008, 60(6):1329-1336.
Katoh, et al., Free-Breathing Renal MR Angiography with Steady-State Free-Precession (SSFP) and Slab-Selective Spin Inversion: Initial Results, Kidney International, 2004, 66:1272-1278.
Katoh, et al., Spin-Labeling Coronary MR Angiography with Steady-State Free Precession and Radial k-Space Sampling: Initial Results in Healthy Volunteers, Radiology, 2005, 236:1047-1052.
Katoh, et al., Local Re-Inversion Coronary MR Angiography: Arterial Spin-Labeling Without the Need for Subtraction, Journal of Magnetic Resonance Imaging, 2008, 27:913-917.
Katoh, et al., Free-Breathing Renal Magnetic Resonance Angiography with Steady-State Free-Precession and Slab-Selective Spin Inversion Combined with Radial k-Space Sampling and Water-Selective Excitation, Magnetic Resonance in Medicine, 2005, 53(5):1228-1233.
Katoh, et al., Flow Targeted 3D Steady-State Free-Precession Coronary MR Angiography: Comparison of Three Different Imaging Approaches, Investigative Radiology, 2009, 44(12):757-762.
Katoh, et al., Flow-Targeted Inversion-Prepared b-TFE Coronary MR Angiography: Initial Results in Patients, Fortschr Rontgenstr, 2009, 181(11):1050-1055.
Keckskemeti, et al., High Resolution Three-Dimensional Cine Phase Contrast MRI of Small Intracranial Aneurysms Using a Stack of Stars k-space Trajectory, Journal of Magnetic Resonance Imaging, 2012, 35(3):518-527.
Kijowski, et al., Vastly Undersampled Isotropic Projection Steady-State Free Precession Imaging of the Knee: Diagnostic Performance Compared with Conventional MR, Radiology, 2009, 251(1):185-194.
Knoll, et al., Fast Reduction of Undersampling Artifacts in Radial MR Angiography with 3D Total Variation on Graphics Hardware, Magn. Reson. Mater. Phy, 2010, 23:103-114.
Korosec, et al., A Data Adaptive Reprojection Technique for MR Angiography, Magnetic Resonance in Medicine, 1992, 24(2):262-274.
Korosec, et al., ECG-Optimized Phase Contrast Line-Scanned MR Angiography, Magnetic Resonance in Medicine, 1992, 24(2):221-235.
Korosec, et al., MR Angiography Using Velocity-Selective Preparation Pulses and Segmented Gradient-Echo Acquisition, Magnetic Resonance in Medicine, 1993, 30(6):704-714.
Korosec, et al., Time-Resolved Contrast-Enhanced 3D MR Angiography, Medical Resonance in Medicine, 1996, 36:345-351.
Korosec, et al., Contrast-Enhanced MR Angiography of the Carotid Bifurcation, Journal of Magnetic Resonance Imaging, 1999, 10(3):317-325.
Kotys, et al., Profile Order and Time-Dependent Artifacts in Contrast-Enhanced Coronary MR Angiography at 3T: Origin and Prevention, Magnetic Resonance in Medicine, 2009, 62(2):292-299.
Lum, et al., Transstenotic Pressure Gradients: Measurement in Swine—Retrospectively ECG-gated 3D Phase-Contrast MR Angiography Versus Endovascular Pressure-Sensing Guidewires, Radiology, 2007, 245(3):751-760.
Mazaheri, et al., Combined Time-Resolved and High-Spatial-Resolution 3D MRA Using an Extended Adaptive Acquisition, Journal of Magnetic Resonance Imaging, 2002, 15(3):291-301.
Mistretta, et al., 3D Time-Resolved Contrast-Enhanced MR DSA: Advantages and Tradeoffs, Magnetic Resonance in Medicine, 1998, 40(4):571-581.
Mistretta, et al., X-Ray Digital Subtraction Angiography to Magnetic Resonance-Digital Subtraction Angiography Using Three-Dimensional TRICKS: Historical Perspective and Computer Simulations, Investigative Radiology, 1998, 33(9):496-505.
Mistretta, et al., Highly Constrained Backprojection for Time-Resolved MRI, Magnetic Resonance in Medicine, 2006, 55(1):30-40.

* cited by examiner

METHOD FOR NON-CONTRAST ENHANCED MAGNETIC RESONANCE ANGIOGRAPHY

CROSS-REFERENCE TO RELATED APPLICATIONS

N/A

BACKGROUND OF THE INVENTION

The field of the invention is magnetic resonance imaging ("MRI") systems and methods and, more particularly, the invention relates to methods for non-contrast enhanced magnetic resonance angiography ("MRA").

When a substance such as human tissue is subjected to a uniform magnetic field (polarizing field $B_0$), the individual magnetic moments of the nuclear spins in the tissue attempt to align with this polarizing field, but process about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) and, related imaging techniques, such as perfusion imaging, use the NMR phenomenon to produce images of the human vasculature or physiological performance related to the human vasculature. There are three main categories of techniques for achieving the desired contrast for the purpose of MR angiography. The first general category is typically referred to as contrast enhanced (CE) MRA. The second general category is phase contrast (PC) MRA. The third general category is time-of-flight (TOF) or tagging-based MRA.

To perform CE MRA, a contrast agent, such as gadolinium, is injected into the patient prior to the magnetic resonance (MR) angiogram to enhance the diagnostic capability of the MR angiogram. Perfusion imaging is employed to assess the viability of tissues. A contrast agent is administered to the subject and a series of MR images are acquired as the contrast agent perfuses into the tissues of interest. From this series of contrast-enhanced MR images hemodynamic parameters such as blood flow, blood volume, and mean transit time may be computed.

While CE MRA is a highly effective means for noninvasively evaluating the vascular and physiological performance, for example, by studying perfusion, the technique suffers from several additional drawbacks. First, the contrast agent that must be administered to enhance the blood vessel carries a significant financial cost. Second, contrast agents such as gadolinium have recently been shown to be causative of a debilitating and potentially fatal disorder called nephrogenic systemic fibrosis (NSF). Third, CE MRA, may not provide accurate or sufficient hemodynamic information, so that it is not always feasible to determine if a stenosis is hemodynamically significant or to assess the perfusion in a clinically useful manner.

Despite strong incentives to move away from CE MRA imaging, current methods for non-contrast angiography are limited in their utility because they are sensitive to patient motion, do not consistently or accurately portray vessel anatomy in patients with severe vascular disease, and require excessively long scan times. For example, while single shot acquisition methods such as two-dimensional ("2D") balanced steady-state free precession ("bSSFP") have the potential to reduce motion artifacts and shorten exam times, arterial conspicuity is inadequate due to high background signal. Moreover, bSSFP methods do not lend themselves to the creation of maximum intensity projection ("MIP") angiograms. In one example, a saturation-recovery bSSFP pulse sequence employed for cardiac perfusion imaging following the administration of a paramagnetic contrast agent is described by W. G. Schreiber, et al., in "Dynamic Contrast-Enhanced Myocardial Perfusion Imaging Using Saturation-Prepared TrueFISP," *JMRI*, 2002; 16:641-652. However, this pulse sequence applies a spatially non-selective saturation pulse that suppresses the signal from blood and, thus, cannot be employed for MRA without contrast material. Additionally, Schreiber's method does not provide a means for distinguishing arteries from veins.

Phase contrast (PC) MRA is largely reserved for the measurement of flow velocities and imaging of veins. Phase contrast sequences are the basis of MRA techniques utilizing the change in the phase shifts of the flowing protons in the region of interest to create an image. Spins that are moving along the direction of a magnetic field gradient receive a phase shift proportional to their velocity. Specifically, in a PC MRA pulse sequence, two data sets with a different amounts of flow sensitivity are acquired. This is usually accomplished by applying gradient pairs, which sequentially dephase and then rephase spins during the sequence. The first data set is acquired using a "flow-compensated" pulse sequence or a pulse sequence without sensitivity to flow. The second data set is acquired using a pulse sequence designed to be sensitive to flow. The amount of flow sensitivity is controlled by the strength of the bipolar gradient pairs used in the pulse sequence because stationary tissue undergoes no effective phase change after the application of the two gradients, whereas the different spatial localization of flowing blood is subjected to the variation of the bipolar gradient. Accordingly, moving spins experience a phase shift. The raw data from the two data sets are subtracted to yield images that illustrate the phase change, which is proportional to spatial velocity. To perform PC MRA pulse sequences, a substantial scan time is generally required and the operator must set a velocity-encoding sensitivity, which varies unpredictably depending on a variety of clinical factors.

Fortunately, TOF imaging techniques do not require the use of a contrast agent and do not rely on potentially-precarious velocity encoding sensitivities. Contrary to CE-MRA, which relies on the administered contrast agent to provide an increase in measured MR signal, TOF MRA relies on the inflow of blood into an imaging volume to increase the signal intensity of the vasculature as compared to the stationary background tissues. This is achieved by the application of a number of RF excitation pulses to the imaging volume that cause the magnetization of the stationary background tissues to reach a saturation value. Since inflowing blood entering the imaging volume is not exposed to the same number of RF excitation, it will provide higher MR signal intensity than the background tissue. The differences between the signal intensity of the stationary background tissues and the inflowing blood thus provide a contrast mechanism exploited by TOF MRA.

In an effort to increase contrast attributable to the relatively small signal levels or weight particular signals, for example, those attributable to cerebral blood flow (CBF) or another measurable mechanism, various "tagging" or "labeling" methods have been developed. One such method is referred to as the arterial spin labeling (ASL) family of techniques. These techniques have been used to detect and provide a quantitative measure of neuronal activity.

Two such methods of non-contrast enhanced MRA are described, for example, by M. Katoh, et al., in "Free-Breathing Renal MR Angiography With Steady-State Free-Precession (SSFP) and Slab-Selective Spin Inversion: Initial Results," *Kidney International,* 2004; 66:1272-1278, and by Y. Yamashita, et al., in "Selective Visualization of Renal Artery Using SSFP with Time-Spatial Labeling Inversion Pulse: Non-Contrast Enhanced MRA for Patients with Renal Failure," *Proc. Intl. Soc. Mag. Reson. Med.* 13 (2005) p. 1715. The method described by Katoh utilizes a three-dimensional ("3D") acquisition with a pre-inversion of the 3D region, while Yamashita employs two inversion pulses (one spatially selective and the other spatially non-selective). Each of these methods uses inversion preparation pulses rather than saturation pulses and further requires the use of a 3D, rather than 2D, acquisition for MRA. Given the substantial thickness of the 3D imaging slab, inflowing unsaturated spins must travel a large distance (for example, up to several centimeters) to replace in-plane saturated ones. Consequently, there is poor depiction of slowly flowing arterial spins. In fact, the inversion time, TI, must be very long (on the order of 1 second) to provide adequate inflow of even moderately fast flowing arterial spins. The long TI spans both the systolic and diastolic phases of the cardiac cycle. Given the long TI, it is problematic to synchronize data acquisition to diastole. In addition, 3D acquisitions are too time-consuming to permit data acquisition within a single breath-holding period.

Unfortunately, TOF and tagging or labeling methods have additional drawbacks. For example, tagging or labeling methods are generally ill suited for dynamic, time-resolved imaging studies designed to produce a visualization, such as a movie, of the flow propagation within the arteries. For example, the large imaging volumes used in 3D labeling techniques result in the inflowing spins becoming saturated across the imaging volume, diminishing attainable image contrast. As such, visualization of the propagation of flow within arteries has traditionally been accomplished with the use of CE MRA or PC MRA. CE MRA has the above-noted drawbacks. Within the context of dynamic, time-resolved angiographic studies, PC MRA is particularly time consuming, typically, requiring a minute of longer to collect one slice location, which precludes rapid imaging of a large vascular territory. Additionally, phase-contrast imaging requires preselection of velocity encoding sensitivity and specialized processing of the phase-information of the MR images; the latter of which is prone to errors stemming from phase aliasing, random phase in regions of low signal intensity, concomitant gradients, and eddy current effects.

Therefore, it would be desirable to have a system and method for performing angiographic studies using MRI systems without the drawbacks presented by CE-MRA, PC-MRA, TOF, or traditional labeling/tagging techniques. Furthermore, it would be desirable to have a system and method for MR angiography that allows the user to image a volume to produce a dynamic or time-resolved series of images of the volume.

SUMMARY OF THE INVENTION

The present invention overcomes the aforementioned drawbacks by providing a system and method for non-enhanced, temporally-resolved MR angiographic images depicting the propagation of blood flow within vessels. The method can be used to generate a dynamic movie or a static angiogram. Though acquiring data from an overall volume of the subject including the vessels, the present invention uses a series of two-dimensional (2D) imaging slices and corresponding tagging slices to acquire a series of undersampled frames using non-Cartesian acquisition. The undersampled frames are retrospectively assembled into at least one of a time-series of images of the vascular structure depicting dynamic flow through the vessels and a static image of the vessels showing improved spatial resolution compared with an individual image reconstructed from a given undersampled image frame in the time-series.

In accordance with one aspect of the invention, a method for non-contrast enhanced magnetic resonance angiography (MRA) of a three-dimensional (3D) volume of a subject having a vascular structure extending through the 3D volume and having flowing spins passing through vascular structure. The method includes applying, with a magnetic resonance imaging (MRI) system, at least one radiofrequency (RF) pulse to a first slice to label the flowing spins passing into a second slice located within the 3D volume adjacent to the first slice. The method also includes acquiring, with the MRI system, imaging data from the second slice using a two-dimensional (2D) pulse sequence and sampling k-space using a non-Cartesian sampling pattern. The method further includes repeating acquisition of the imaging data to acquire a series of second slices located across the 3D volume to acquire respective sets of imaging data spanning the 3D volume. The sets of imaging data are reconstructed into a time-series of image frames depicting the flowing spins passing through the vascular structure.

In accordance with another aspect of the invention, a magnetic resonance imaging (MRI) system includes a magnet system configured to generate a polarizing magnetic field about at least a portion of a subject arranged in the MRI system and a plurality of gradient coils configured to apply a gradient field to the polarizing magnetic field. The MRI system further includes a radio frequency (RF) system configured to apply an excitation field to the subject and acquire MR image data therefrom and a computer system. The computer system is programmed to control the RF system to label flowing spins passing through a first slice located within a 3D volume in a subject being imaged and control the RF system and plurality of gradient coils to acquire imaging data from a second slice proximate to the first slice using a two-dimensional (2D) pulse sequence and a non-Cartesian k-space sampling pattern. The computer is further programmed to control the RF system and the plurality of gradient coils to acquire a series of second slices located across the 3D volume to acquire respective sets of imaging data spanning the 3D volume and reconstruct the sets of imaging data into a time-series of image frames depicting the flowing spins passing through the vascular structure.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
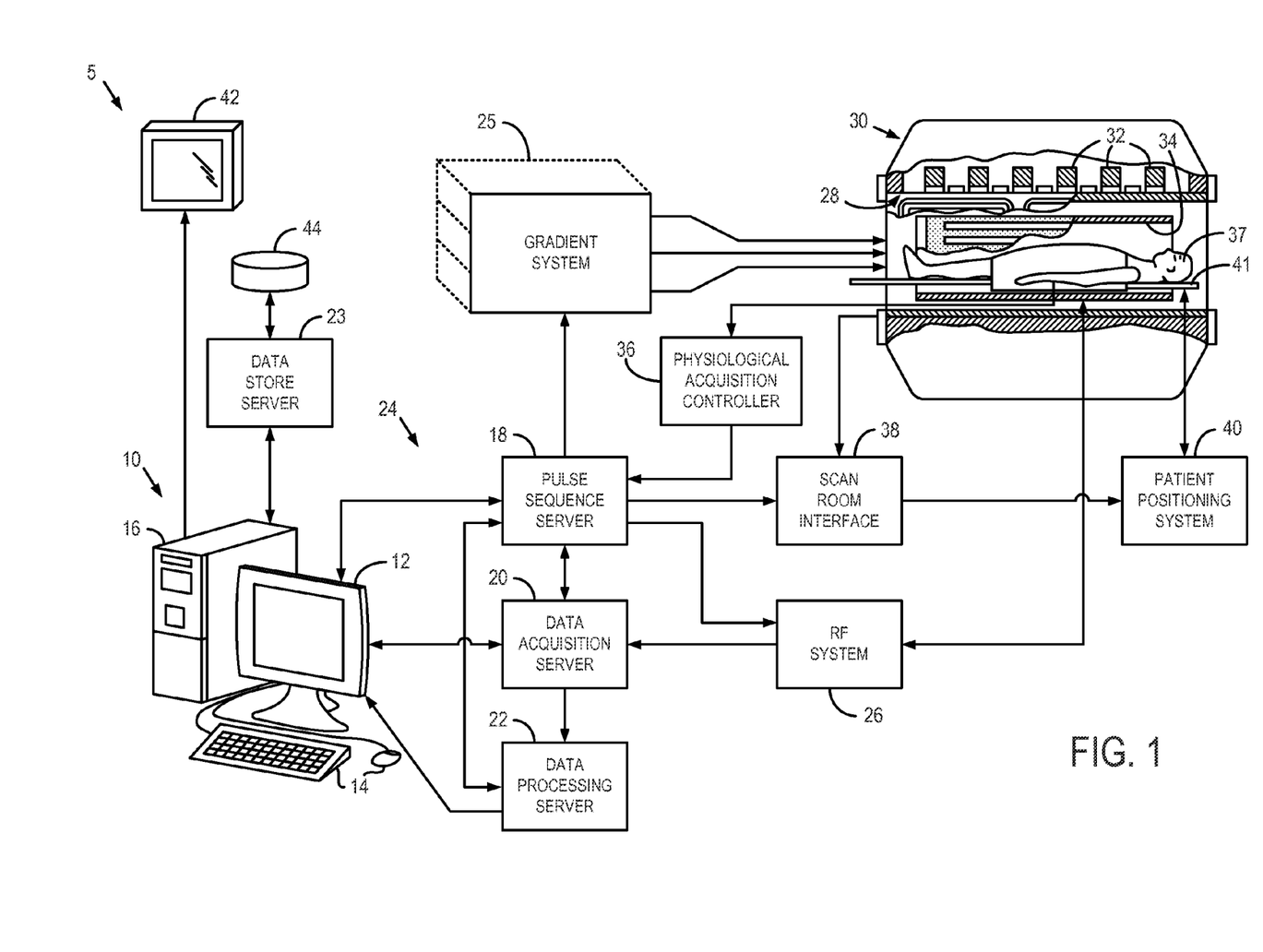
FIG. 1 is a block diagram of an MRI system that employs the present invention.

Referring particularly to FIG. 1, the invention is employed in an MRI system 5. The MRI system 5 includes a workstation 10 having a display 12, a user interface 14, and a processor 16. The workstation 10 provides the operator interface that enables scan prescriptions to be entered into the MRI system. The workstation 10 is coupled to, for example, four servers, including a pulse sequence server 18, a data acquisition server 20, a data processing server 22, and a data store server 23. In one configuration, the data store server 23 is performed by the workstation processor 16 and associated disc drive interface circuitry and the remaining three servers 18, 20, 22 are performed by separate processors mounted in a single enclosure and interconnected using a backplane bus.

The workstation 10 and each processor for the servers 18, 20, 22, and 23 are connected to a communications network 24. This network conveys 24 data that is downloaded to the servers 18, 20, 22, 23 from the workstation 10 and conveys data that is communicated between the servers 18, 20, 22, 23 and between the workstation 10 and the servers 18, 20, 22, 23. In addition, a high speed data link may be provided between the data processing server 22 and the workstation 10 in order to convey image data to the data store server 23.

The pulse sequence server 18 functions in response to program elements downloaded from the workstation 10 to operate a gradient system 25 and an RF system 26. Gradient waveforms necessary to perform the prescribed scan are produced and applied to the gradient system 25 that excites gradient coils arranged about an bore 28 to produce the magnetic field gradients $G_x$, $G_y$, and $G_z$ used for position encoding NMR signals. The gradient system 25 forms part of a magnet assembly 30, which includes a polarizing magnet 32 and a whole-body RF coil 34.

The RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase, and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector that detects and digitizes the in-phase (I) and quadrature (Q) components of the received NMR signal. The magnitude of the received NMR signal may thus be determined at any sampled point by the square root of the sum of the squares of the I and Q components.

The pulse sequence server 18 also optionally receives patient data from a physiological acquisition controller 36. The controller 36 receives signals from a number of different sensors connected to the patient 37, such as ECG signals from electrodes or respiratory signals from a bellows.

The pulse sequence server 18 also connects to a scan room interface circuit 38 that receives signals from various sensors associated with the condition of the patient 37 and the magnet system. It is also through the scan room interface circuit 38 that a patient positioning system 40 receives commands to move the patient 37 to desired positions during the scan by moving a patient table 41.

It should be apparent that the pulse sequence server 18 performs real-time control of MRI system elements during a scan. As a result, its hardware elements are generally operated according to program instructions that are executed in a timely manner by run-time programs. The description components for a scan prescription are downloaded from the workstation 10 in the form of objects. The pulse sequence server 18 contains programs that receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans, the data acquisition server 20 does little more than pass the acquired NMR data to the data processor server 22. However, in scans that require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. Furthermore, the data acquisition server 20 may be employed to process NMR signals used to detect the arrival of contrast agent in an MRA scan. In all these examples the data acquisition server 20 acquires NMR data and processes it in real-time to produce information that is used to control the scan.

The data processing server 22 receives NMR data from the data acquisition server 20 and processes it in accordance with description components downloaded from the workstation 10. Such processing may include, for example, Fourier transformation of raw k-space NMR data to produce two or three-dimensional images, the application of filters to a reconstructed image, the performance of a backprojection image reconstruction of acquired NMR data, the calculation of functional MR images, the calculation of motion or flow images, and the like.

Images reconstructed by the data processing server 22 are conveyed back to the workstation 10. Real-time images are stored in a database (not shown) from which they may be output to operator display 12 or a display 42 that is located remotely, such as near the magnet assembly 30 for use by attending physicians. Batch mode images or selected real time images are stored in a host database on disc storage 44. When such images have been reconstructed and transferred for storage, the data processing server 22 notifies the data store server 23 on the workstation 10. The workstation 10 may be used by an operator to archive the images, produce films, or send the images via a network to other facilities.

Figure 2A:
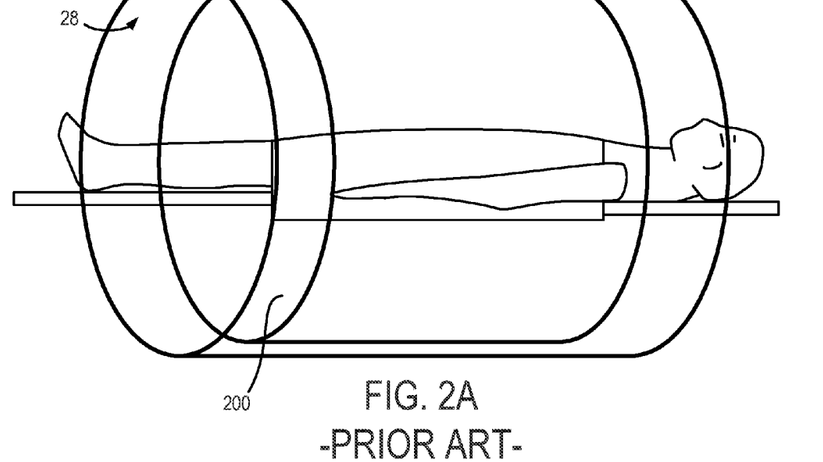
FIGS. 2A and 2B are a pictorial representation of a prior-art method for acquiring magnetic resonance angiography (MRA) data from a subject using a three-dimensional (3D) imaging technique.

The MRI system 10 described above with respect to FIG. 1 may be utilized to carry out a variety of medical imaging processes. As previously discussed, one common clinical application for such MRI system 10 is magnetic resonance angiography (MRA). With MRA applications, one desired clinical application is the acquisition of MRA data from a three-dimensional (3D) volume over a period of time to then create a time series of images that can be viewed as a movie to show the propagation of flow in the vessels within the 3D volume. Referring to FIG. 2A, traditional strategies for acquiring data MRA from such a 3D volume typically rely on exciting a large volume 200 including the 3D volume of interest and acquiring data from the volume 200 using a 3D pulse sequence.

Figure 2B:
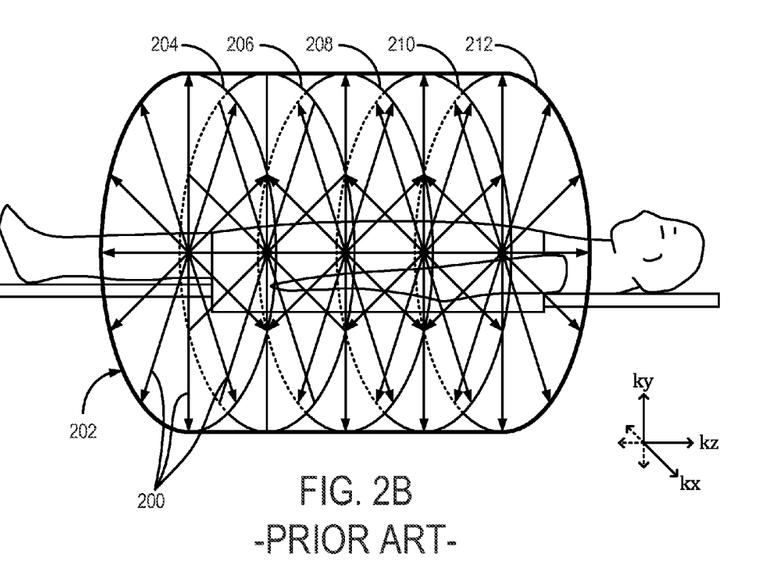

As illustrated in FIG. 2B, in some cases the pulse sequence may employ radial or projection imaging sequence that is reflected as a so-called stack-of-stars acquisition 202. The stack-of-stars acquisition 202 refers to a 3D imaging scan where radial samplings 204, 206, 208, 210, 212 are performed to acquire the kx-ky space, and traditional phase-encoding is used in the slice-select, (kz) direction. Such 3D radial phase-encoded sequences are often gradient-recalled MR echo sequences. Variations on the basic stack-of-stars concept add further complexity and have been specifically-tailored to phase-contrast (PC) MRA acquisitions. For example, PC vastly undersampled isotropic projection (PC VIPR) pulse sequences have been used to generate isotropic angiographic images. Unfortunately, these methods suffer, as described above, from drawbacks such as complex planning for the velocity encoding required for phase contrast imaging, long acquisition times associated with 3D imaging, substantial saturation of inflowing spins across the imaging volume, substantial susceptibility to motion artifacts, and many other drawbacks.

Turning to FIGS. 3A-3D, the present invention utilizes a 2D acquisition without slice-encoding and acquires a series of 2D slices to image a 3D volume. That is, a series of 2D acquisitions is performed to acquire image data from a 3D volume. The 2D acquisitions may be cardiac gated. To acquire information from flows propagating in the vessels within the 3D volume, labeling or tagging techniques may be coupled with each 2D slice acquisition. These labeling or tagging techniques utilize RF pulses, dephasing gradient pulses, and/or other techniques in varying amplitudes and implementations to elicit or suppress signal from spins flowing in the vascular and/or vary signal based on flow velocity. Exemplary pulse sequences used for 2D imaging may include the so-called balanced steady-state free precession (bSSFP) pulse sequence, pulse sequences utilizing the "quiescence interval" (QI)," such as the quiescent interval steady-state (QISS) and those described in co-pending patent application Ser. Nos. 12/574,856 and 13/026,482, which are incorporated herein by reference in its entirety, and the like.

Figure 3A:
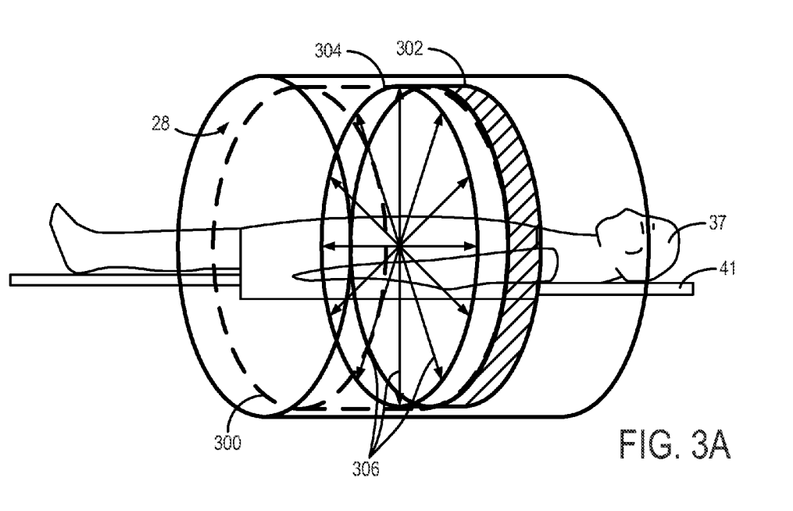
FIGS. 3A-3D are a pictorial representation of a two-dimensional (2D) imaging technique for imaging a volume of a subject over a 3D volume performed by the MRI system of FIG. 1 when practicing an embodiment the present invention.
Figure 4:
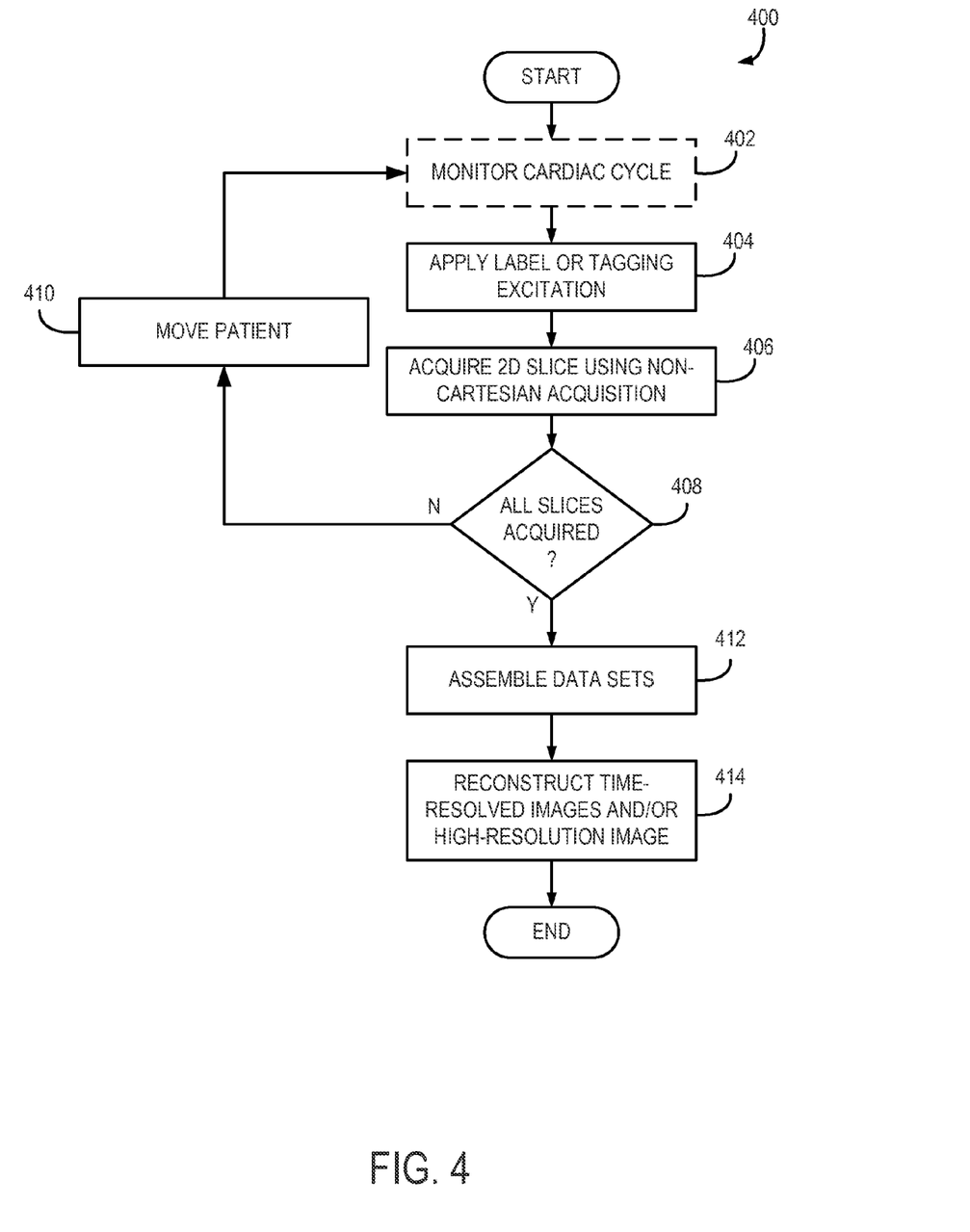
FIG. 4 is a flow chart setting forth exemplary steps of a method in accordance with the present invention.

Referring to FIGS. 3A and 4, a process 400 in accordance with the present invention begins at process block 402 by monitoring the cardiac cycle of the patient 37, such as using imaging or non-imaging means, including EKG or other monitoring. The process 400 continues at process block 404 with a radiofrequency (RF) pulse or pulses being applied to suppress spins in one or more regions of an overall 3D volume of interest 300 during one or more portions of the cardiac cycle. That is, a label or tagging excitation is applied to a first slice 302 to suppress the signal intensity of blood vessels and/or background tissue. After the application of the label or tagging excitation to the first slice 302 at process block 406, one or more 2D non-Cartesian acquisitions are performed to acquire imaging data from a second slice 304 at process block 406. As will be further described, the first slice 302 and second slice 304 are proximate to one another and, in some cases, may overlap or partially overlap one another. In any case, process block 404 and 406 may be performed together as a 2D pulse sequence or, alternatively, process block 404 may be intermittently or separately performed from the pulse sequence used to acquire the 2D slice at process block 406.

Figure 5A:
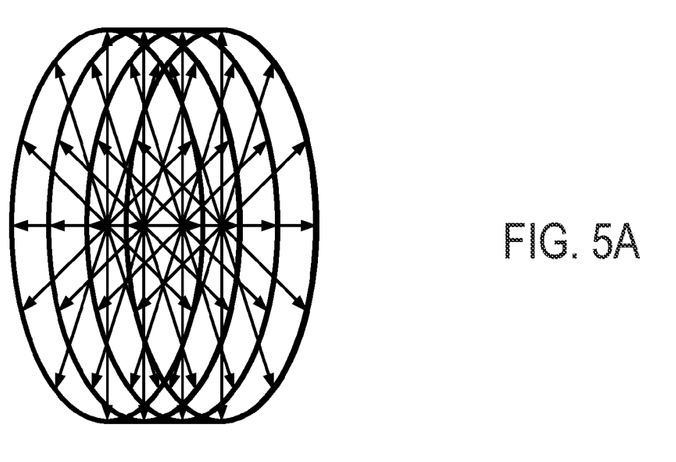
FIGS. 5A and 5B are pictorial representation of non-Cartesian k-space sampling techniques in accordance with the present invention.
Figure 5B:
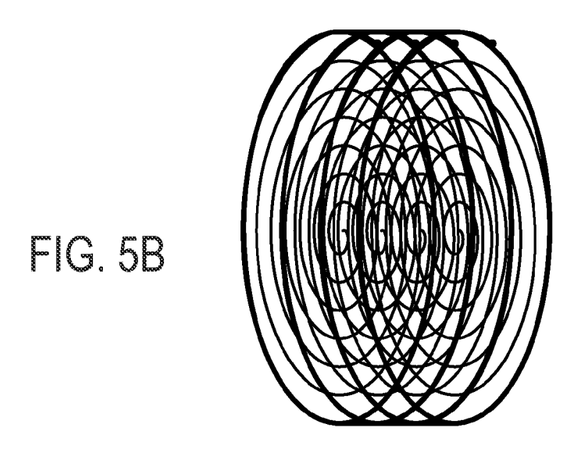

As illustrated in FIGS. 3A, 5A, and 5B, the non-Cartesian acquision of the second slice 304 may be achieved by way of a series of radial or projection samples 306. However, while projections are illustrated in FIGS. 3A and 5A, a variety of other non-Cartesian k-space sampling patters are contemplated, including spiral, as illustrated in FIG. 5B, and the like. The 2D non-Cartesian acquisition of the second slice 304 may span a substantial portion of the cardiac cycle, but can be acquired with substantial undersampling and, thereby, over a comparatively short duration when compared, for example, with non-undersampled projection imaging or 3D samplings.

Figure 3B:
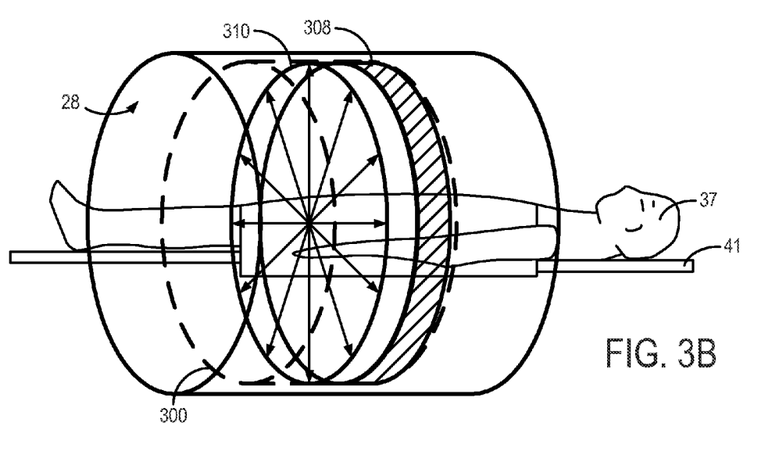
Figure 3C:
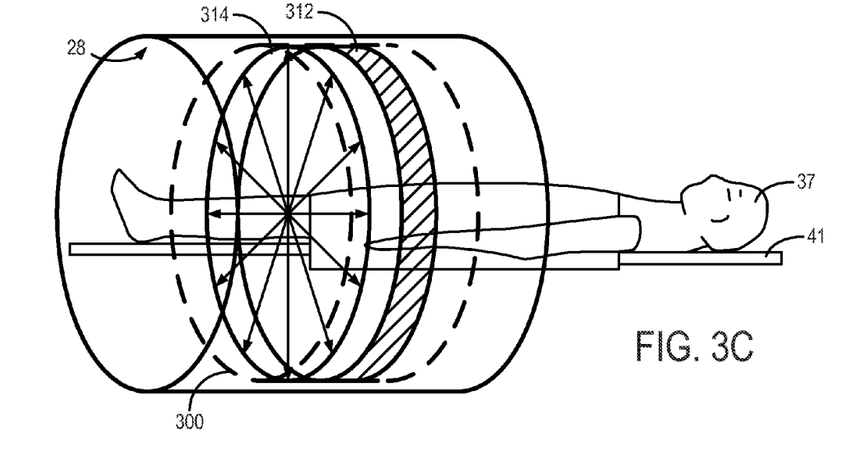
Figure 3D:
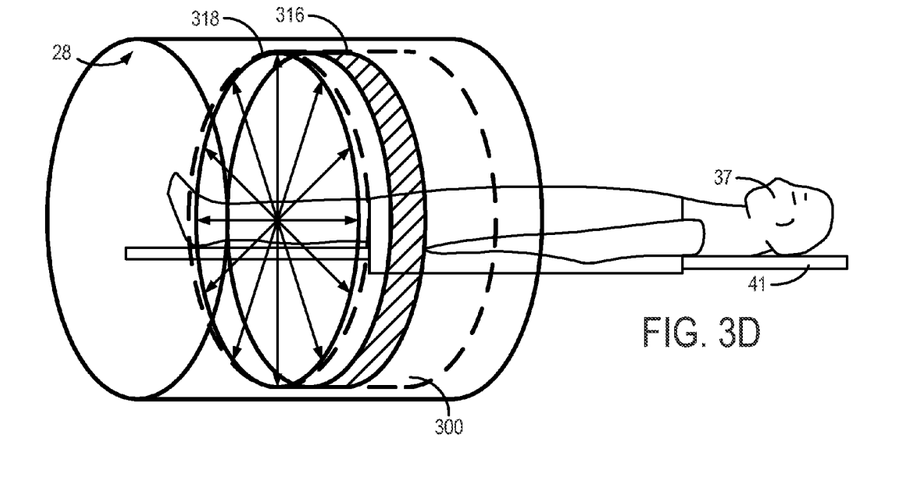

Referring now to FIGS. 4 and 3B-3D, this process is repeated at decision block 408 to acquire data from the entire 3D volume of interest 300. That is, additional slices are acquired so as to create a stack of contiguous or overlapping time-resolved images of blood vessels over the cardiac cycle. Specifically, as illustrated in FIGS. 3A-3B and 4, to acquire a subsequent 2D slice, the patient 37 may be moved relative to the bore 28 using the patient table 41, as indicated a process block 410, to position a subsequent label or tagging excitation to a first slice 308 and associated non-Cartesian acquisition of a second slice 310 at or proximate to the isocenter of the MR system. As mentioned, doing so ensures the greatest homogeneity and SNR across the FOV and, thus, yields many benefits, such as improved fat suppression and the like. As illustrated in FIGS. 3C and 3D, this process is repeated to perform subsequent labeling or tagging excitations in selected slices 312, 316 and data acquisitions at selected slices 314, 318 until a sufficient number of slices have been acquired 304, 310, 314, 318 to collectively cover the whole 3D volume of interest 300.

Once all slices have been acquired, the data sets may be assembled at process block 412 to then reconstruct, at process block 414, either or both of a time-resolved set of images, such as a cine dynamic angiographic movie, or a static high spatial resolution image. The above-referenced stacks of images can be reprojected so as to display an MR angiogram, and the time-resolved frames viewed in a movie loop to display the propagation of blood flow within the cardiac cycle. As an additional option, a static angiogram of the entire vascular territory may be generated by reconstructing a large fraction of the acquired radial projections. Thus, subsets of acquired data may be reconstructed to create a series of time-resolved images of vessels of interest over the cardiac cycle or may be combined to create a static angiogram of the entire vascular territory.

Advantageously, assembling the data sets allows retrospective selection of advantageous imaging parameters and data groupings. For example, retrospective selection can be used to selectively reconstruct data associated with particular portions of the cardiac cycle. Furthermore, specific, desired projections can be combined, even spanning multiple data sets, to create images. Furthermore, imaging parameters, such as a desired inflow or interval time (TI) between the label or tagging slices 302 and 2D non-Cartesian imaging slices 304, QI, and the like may be selected retrospectively.

Thus, the present invention utilizes 2D acquisition without slice-encoding and acquires a series of 2D slices to, as will be explained, image a volume. That is, a series of 2D acquisitions is performed to acquire image data from a 3D volume. The 2D acquisitions may be cardiac gated. To acquire information from flows propagating in the vessels within the 3D volume, labeling or tagging techniques may be coupled with each 2D slice acquisition. Specifically, radiofrequency (RF) pulse(s) may be applied to one or more regions of the overall 3D volume of interest during one or more portions of the cardiac cycle so as to suppress the signal intensity of blood vessels and background tissue. After the application of the RF pulse, one or more 2D non-Cartesian acquision are performed and may span a substantial portion of the cardiac cycle. After this process has been repeated to acquire data from the 3D volume of interest, subsets of data can be reconstructed to create a series of time-resolved images of vessels of interest over the cardiac cycle or may be combined to create a static angiogram of the entire vascular territory.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for non-contrast enhanced magnetic resonance angiography (MRA) of a three-dimensional (3D) volume of a subject having a vascular structure extending through the 3D volume and having flowing spins passing through vascular structure, the method comprising the steps of:
   a) applying, with a magnetic resonance imaging (MRI) system, at least one radiofrequency (RF) pulse to a first slice to label the flowing spins passing into a second slice located within the 3D volume adjacent to the first slice;
   b) acquiring, with the MRI system, imaging data from the second slice using a two-dimensional (2D) pulse sequence and sampling k-space using a non-Cartesian sampling pattern;
   c) repeating steps a) and b) to acquire a series of second slices located across the 3D volume to acquire respective sets of imaging data spanning the 3D volume; and
   d) reconstructing the sets of imaging data into a time-series of image frames depicting the flowing spins passing through the vascular structure.

2. The method of claim 1 wherein step c) includes moving the subject through a series of imaging locations to acquire the series of second slices located across the 3D volume.

3. The method of claim 2 wherein the second imaging slice, after each move, is located proximate to an isocenter of the MRI system.

4. The method of claim 1 wherein the non-Cartesian sampling pattern includes at least one of radial and spiral sampling.

5. The method of claim 1 further comprising e) reconstructing a static 2D image of the 3D volume using the sets of imaging data.

6. The method of claim 1 wherein step d) includes selecting portions of the imaging data within the sets of imaging data to reconstruct the image frames therefrom.

7. The method of claim 1 wherein step d) includes selecting imaging parameters retrospectively.

8. The method of claim 1 wherein the second slices located across the 3D volume are positioned to be at least partially overlapping.

9. The method of claim 1 further comprising monitoring a cardiac cycle of the subject and coordinating steps a) through c) within the cardiac cycle of the subject.

10. The method of claim 1 wherein the imaging data acquired in steps c) and d) is acquired without a predetermined flow sensitivity.

11. The method of claim 1 wherein step b) includes exciting only the second slice to acquire imaging data from the second slice.

12. The method of claim 1 wherein steps a) and b) are performed together as a 2D pulse sequence.

13. A magnetic resonance imaging (MRI) system comprising:
   a magnet system configured to generate a polarizing magnetic field about at least a portion of a subject arranged in the MRI system;
   a plurality of gradient coils configured to apply a gradient field to the polarizing magnetic field;
   a radio frequency (RF) system configured to apply an excitation field to the subject and acquire MR image data therefrom;
   a computer system programmed to:
      control the RF system to label flowing spins passing through a first slice located within a 3D volume in a subject being imaged;
      control the RF system and plurality of gradient coils to acquire imaging data from a second slice proximate to the first slice using a two-dimensional (2D) pulse sequence and a non-Cartesian k-space sampling pattern;
      control the RF system and the plurality of gradient coils to acquire a series of second slices located across the 3D volume to acquire respective sets of imaging data spanning the 3D volume; and
      reconstruct the sets of imaging data into a time-series of image frames depicting the flowing spins passing through the vascular structure.

14. The system of claim 13 further comprising a patient table configured to support the subject being imaged and configured to move the patient through a plurality of positions within the MRI system and wherein the computer system is further programmed to move the patient table during acquisition of the series of second slices to locate each second slice proximate to an isocenter of the MRI system.

15. The system of claim 13 wherein the computer system is further programmed to utilize at least one of radial and spiral sampling as the non-Cartesian sampling pattern.

16. The system of claim 13 wherein the computer system is further programmed to reconstruct a static 2D image of the 3D volume using the sets of imaging data.

17. The system of claim 13 wherein the computer system is programmed to select portions of the imaging data within the sets of imaging data to reconstruct the image frames therefrom.

18. The system of claim 13 wherein the computer system is further programmed to control the RF system and plurality of gradient coils to position the second slices located across the 3D volume to be at least partially overlapping.

19. The system of claim 13 further comprising a cardiac monitoring system configured to monitor a cardiac cycle of the subject and wherein the computer system is configured to coordinate control of the RF system and plurality of gradient coils to acquire data from the subject at predetermined periods within the cardiac cycle of the subject.

20. The system of claim 13 wherein the computer system is further configured to acquire the imaging data without a predetermined flow sensitivity.

21. The system of claim 13 wherein the computer system is further configured to control the RF system and plurality of gradient coils to excite only the second slice and acquire imaging data from the second slice.

22. The system of claim 13 wherein the first slice and the second slice at least partially overlap.

\* \* \* \* \*

UNITED STATES PATENT AND TRADEMARK OFFICE
CERTIFICATE OF CORRECTION

PATENT NO. : 8,744,551 B2  
APPLICATION NO. : 13/547699  
DATED : June 3, 2014  
INVENTOR(S) : Ioannis Koktzoglou and Robert R. Edelman Page 1 of 1

It is certified that error appears in the above-identified patent and that said Letters Patent is hereby corrected as shown below:

In the Specification

Column 1, line 18 "process" should be -- precess --

Signed and Sealed this  
Twenty-sixth Day of August, 2014

Michelle K. Lee  
*Deputy Director of the United States Patent and Trademark Office*